United States Patent [19]
McCartan et al.

[11] Patent Number: 5,995,348
[45] Date of Patent: Nov. 30, 1999

[54] GROUND SAFETY DEVICE FOR MEDICAL ULTRASOUND PROBES

[75] Inventors: Dermot McCartan, Tullymore Benburb, Ireland; John D. Marshall, Redwood City; David L. Lidgey, Dublin, both of Calif.

[73] Assignee: Acuson Corporation, Mountain View, Calif.

[21] Appl. No.: 08/934,042

[22] Filed: Sep. 19, 1997

[51] Int. Cl.[6] .................................................. H02H 3/00
[52] U.S. Cl. ............................. 361/42; 361/45; 361/115
[58] Field of Search ............................ 361/42, 45, 58, 361/91, 115

[56] References Cited

U.S. PATENT DOCUMENTS

| 3,590,322 | 6/1971 | Carr | 361/42 |
|---|---|---|---|
| 4,535,759 | 8/1985 | Polk et al. | 128/24 A |
| 4,546,401 | 10/1985 | Svedberg | 361/91 |
| 4,744,369 | 5/1988 | Kroll | 128/696 |
| 4,811,156 | 3/1989 | Kroll | 361/59 |

*Primary Examiner*—Stephen W Jackson
*Attorney, Agent, or Firm*—Brinks Hofer Gilson & Lione

[57] ABSTRACT

An electronic device placed in series with the probe ground-to-chassis connection. The device comprises a current-detecting element such as a resistor or RC network and may employ frequency-discriminating circuitry to limit only ground current signals below a certain frequency. The detector element triggers either a current limiter or a latching switch to prevent currents exceeding about 20 $\mu$A rms from flowing between the probe and the patient. This is achieved by limiting such currents dynamically or by latching the transducer-probe-ground/system-chassis connection in an "open" state. In normal operation, the limiting/latching function is inactive, i.e. it is transparent to the system and the device shunts noise signals to the system chassis to prevent image degradation. The resistance of the device in normal operation may be in the range of about 0.1 to 10 ohms for effective noise reduction (shielding) at operating frequencies at and above 100 kHz. Preferably, the insertion resistance is about 2 ohms or less. Upon detection of an overcurrent event, the hardware may additionally be configured to notify the imaging system of the potential hazard. The imaging system may, in turn, display a warning message on its screen, and/or it may lock out further use of the system. The system may also be configured to reset the transducer-probe-ground/system-chassis connection and the current detector via software control after the single-fault condition abates.

44 Claims, 5 Drawing Sheets

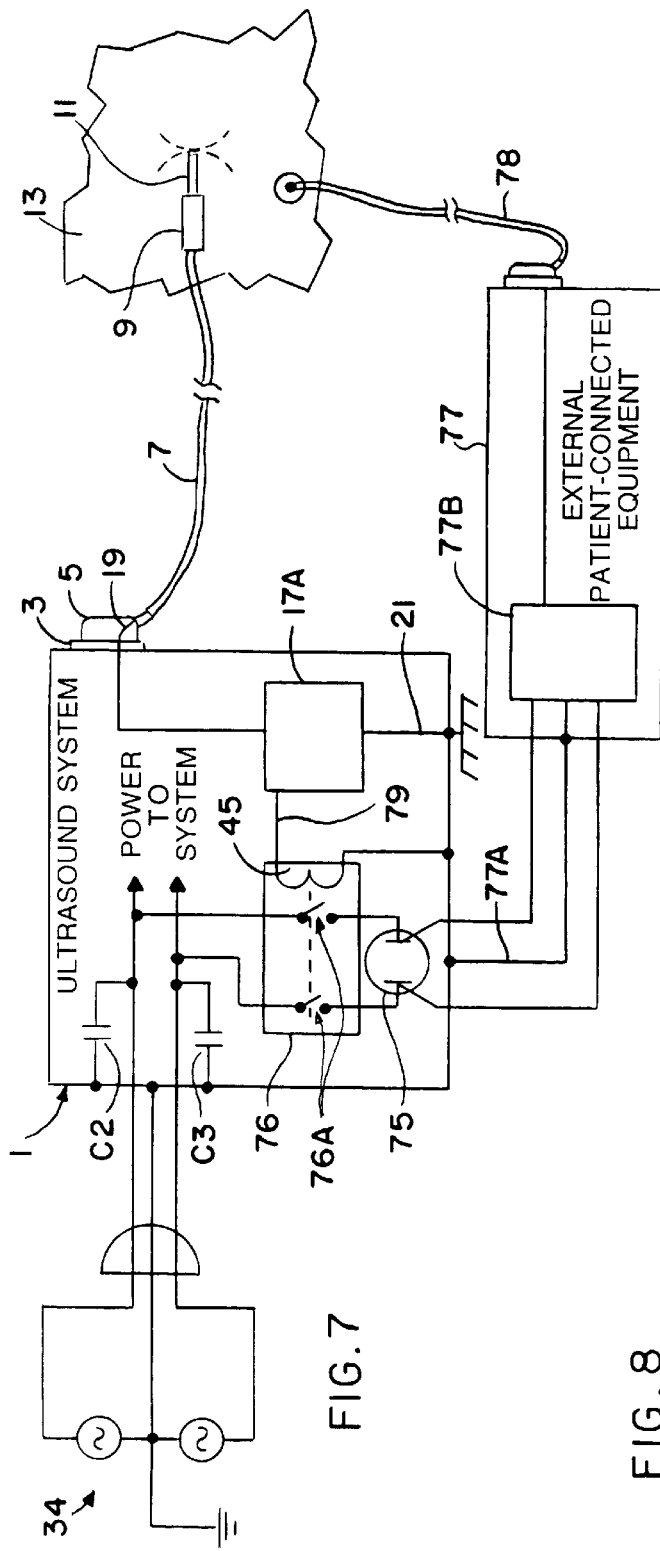
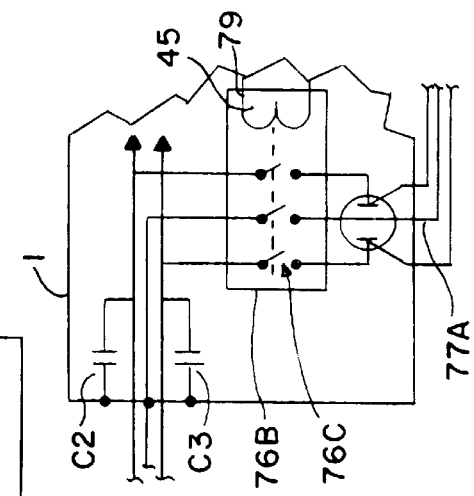
FIG. 7
FIG. 8
FIG. 9

GROUND SAFETY DEVICE FOR MEDICAL ULTRASOUND PROBES

BACKGROUND OF THE INVENTION

1. Field of the Invention

This invention relates to a safety device for medical electrical apparatus, and in particular to such apparatus for limiting current coupled to a body from an ultrasound transducer probe.

2. Brief Description of the Prior Art

Medical ultrasound probes tend to pick up electrical noise via capacitance coupled between the internal probe wiring and the body of the patient. This noise is particularly severe in probes designed for insertion into a body cavity (e.g., transesophageal probes, endocavity probes, laparoscopic probes, and catheter probes), because their contact surface area, and consequently their coupling capacitance, is larger than that in probes applied to the outside of the body.

The electrical noise is typically greatly reduced by adding an outer conductive ground shield to the insertable portion of the probe. The shield itself is insulated from the patient by a dielectric cover or housing and thus has its own coupling capacitance to the body. Often, the shield also adds mechanical strength to the probe, especially to a catheter probe. The shield is electrically connected to the ultrasound system chassis and prevents noise signals from degrading the ultrasound image by shunting them to system ground.

This noise reduction technique is well known and is effective in many situations, but has a major drawback. The coupling capacitance, whether it is associated with the internal probe wiring or with an outer ground shield, is also responsible for potentially dangerous leakage currents arising from a single-fault condition in the ultrasound system, or in another device already placed within the body. Underwriters Laboratories (UL) regulations require that the leakage current not exceed 20 $\mu$A rms (see UL 544, Section 42.4.1).

The UL requirement is usually met by reducing the capacitive coupling between the chassis-grounded internal probe components and the patient. That is, the thickness of the insulating outer cover or housing is increased and/or the spacing between the internal current carrying components of the probe and the body is increased. This solution is difficult to implement in insertable probes, and particularly so in small diameter devices such as catheter probes where the insulation thickness must be kept to a minimum.

Prior art methods include:

1) Tolerate the coupling noise—do not compromise patient safety;
2) Increase insulation thickness to reduce coupling capacitance—use an outer shield if possible; and
3) Adjust the ultrasound system response to attenuate the frequency range containing the coupled noise.

Disadvantages of the prior art methods include:

1) Electrical noise sources common in the hospital environment can be severe enough to render ultrasound imaging ineffective, misleading, or useless; and
2) Probes can become unwieldy because of attempts to reduce the coupling capacitance by increasing the probe wall thickness.

SUMMARY OF THE INVENTION

The present invention solves the shield ground current problem by placing an electronic device in series with the probe shield-to-chassis connection. The device comprises a current-detecting element such as a resistor and may employ frequency-discriminating circuitry to limit only shield ground current signals below a certain frequency. The detector element triggers either a current limiter or a latching switch or contact arrangement to prevent currents exceeding about 15 to 20 $\mu$A rms from flowing between the probe and the patient. This is achieved by limiting such currents dynamically or by latching the transducer-probe-shield/system-chassis connection in an "open" state. In normal operation, the limiting/latching function is inactive, i.e. it is transparent to the system and the device shunts noise signals to the system chassis to prevent image degradation. Theoretically, the resistance of the shield ground safety device should be 0 ohms. However, practically, the resistance of the device in normal operation may be in the range of about 0.1 to 10 ohms for operating frequencies at and above 100 kHz for effective reduce noise reduction (shielding). Preferably, the insertion resistance is about 2 ohms or less. Typically, using the disclosed embodiments of the invention or obvious variants thereof, the insertion resistance of the device in normal operation is about 1 ohm.

In addition to the immediate disconnection of the probe shield ground upon detection of an overcurrent event, the hardware is configured to notify the imaging system of the potential hazard. The imaging system may, in turn, display a warning message on its screen, and/or it may lock out further use of the system. The system may also be configured to reset the transducer-probe-shield/system-chassis connection and the current detector via software control after the single-fault condition abates.

As noted above, preferably a probe shield is built into the insertable length of the probe. The shield is insulated from patient contact in such a way that the coupling capacitance is made as low as possible, that is, with the thickest insulator that is practicable. In order to keep ground currents from exceeding 20 $\mu$A, the probe shield is connected to the chassis of the ultrasound system via an electronic device of one of the following four constructions.

1) An active network that is transparent to ground current signals if they are lower than a certain prescribed threshold, and limits ground current signals which exceed the threshold.

2) An active network (cf the network in U.S. Pat. Nos. 4,744,369 and 4,811,156 to Kroll) that is transparent to ground current signals if they are lower than a certain prescribed threshold, but rapidly latches in an "open" state when the active network senses a ground current signal exceeding the threshold.

It is to be noted that the devices according to the Kroll patents are not suitable for use in shielding ultrasound probes, because their "on" resistance is too high, typically 50k to 500k ohms. The present invention has an "on" resistance of about 0.1 to 10 ohms for operating frequencies at and above 100 kHz.

Reference is also made to U.S. Pat. No. 4,546,401 to Svedberg which proposes a monolithic silicon device to accomplish this function. However, the device of Svedberg has limitations. In particular, the device depends on the onset of high injection in one junction of a thyristor device to set its threshold current. This arrangement works well if the threshold is fairly high, i.e. on the order of 50 to 500 milliamps, but it is unsuitable for the low-current device (10 to 20 microamps) to meet the UL regulations for ultrasound transducers.

Further, Svedberg's device requires a moderate voltage (about 1 to 1.4 volts) to be applied across its terminals to initiate conduction. This level of voltage could not be supplied by an acoustic transducer device, and thus Svedberg's device could not be employed in such applications.

Yet further, the off-state current through Svedberg's device is limited only by a JFET with its gate connected to its drain; this current is likely to be greater than the UL regulated 20 microamp limit.

3) An active network that is transparent to ground current signals having an alternating current (AC) content substantially above a predetermined cutoff frequency, but strongly limits ground current signals with AC content below the cutoff frequency.

It should be noted that a properly chosen capacitor may work in some applications, but not for the purposes of the present invention. For example, the capacitance must be less than about 440 pF to meet the leakage requirement at 60 Hz, but it must be greater than or about 75 nF to be an effective shunt at 1 MHz.

4) An active network that is transparent to ground current signals having an AC content exclusively above a predetermined cutoff frequency, but rapidly latches in an "open" state when it senses an appreciable ground current signal below its cutoff frequency.

BRIEF DESCRIPTION OF THE DRAWING

These and other aspects of the invention will be better understood, and additional features of the invention will be described hereinafter having reference to the accompanying drawings in which:

FIG. 7 is a schematic block diagram showing an external patient-connected equipment unit power connected to an ultrasound system console and signal connected to a body in contact with a transducer probe;

FIG. 8 is a block diagram showing the major components of yet another embodiment of shield ground safety device when associated with an external patient-connected equipment unit; and FIG. 9 is a schematic diagram showing an alternate form of the power connection between an ultrasound system and an external patient-connected equipment unit.

DETAILED DESCRIPTION OF THE PREFERRED EMBODIMENTS

Figure 1A:
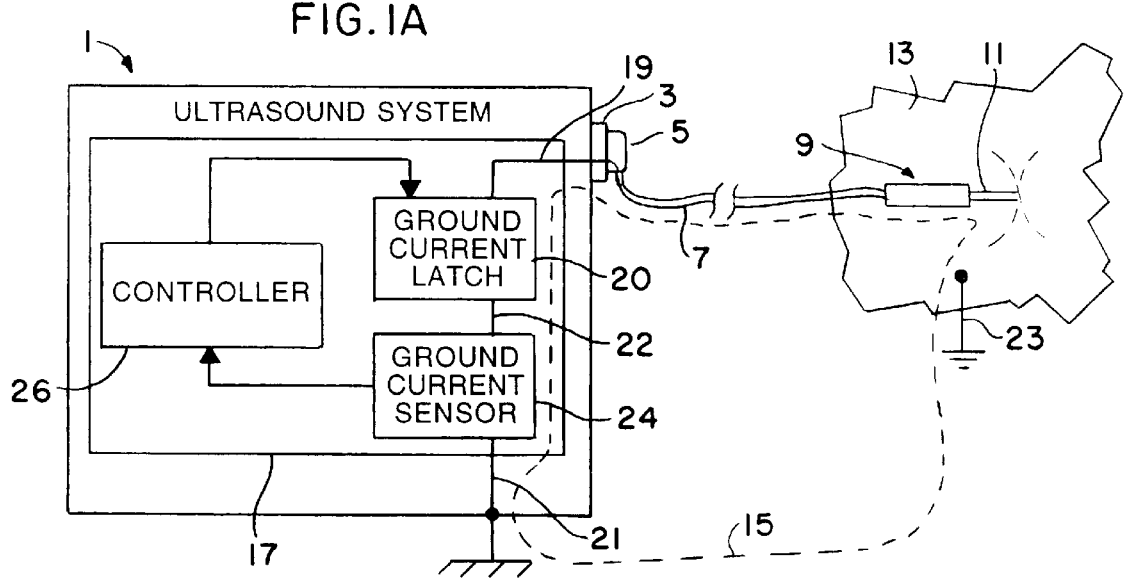
FIG. 1A is a block diagram representation of an ultrasound transducer probe inserted into a body cavity and connected electronically to an ultrasound system console containing the shield ground safety device according to the present invention.

FIG. 1A is a block diagram representation of an ultrasound system 1 having a multi-pin receptacle 3. A complementary multi-pin plug 5 is connected at one end of a multi-conductor grounded (e.g., shielded) cable 7, cable 7 being connected at its other end to an ultrasound transducer probe 9. The transducer probe 9 may be any of a variety of medical probes designed for insertion into a body cavity including, but not limited to, transesophageal probes, endocavity probes, laparoscopic probes, and catheter probes. Shown by way of example only are a pencil-sized rigid probe shown in FIGS. 1 and 2, and a thin catheter probe shown in FIG. 3. It is to be understood, however, that the present invention may be utilized in an ultrasound system arrangement employing transducers of a number of different designs, those shown in the accompanying figures being exemplary only. In any event, the insertable portion 11 of the probe 9 is shown in FIG. 1A to be inserted into a body cavity in a body 13.

As suggested previously, AC ground currents may flow in a ground current path 15, from the system ground 21 through shield ground conductor 19, the ground shield of cable 7, the ground shield of probe 9, and through the body 13 to space ground 23. Without the ground current limiter 20 and ground current sensor 24 in series with the ground conductor 19 and ultrasound system ground 21, dangerous currents may flow in AC ground current path 15 due to unwanted, but occasionally generated, single-fault conditions in the ultrasound system arrangement. It is the object of the present invention to limit the AC ground current flowing in path 15 or to interrupt the flow of AC ground current when the magnitude of the AC ground current exceeds a predetermined threshold, namely 20 $\mu$A.

This objective is accomplished according to the general scheme shown in FIG. 1A by the provision of a shield ground safety device 17. In one embodiment of the invention, a ground current latch 20 is in series with the ground conductor 19 from the transducer receptacle/plug connector 3,5 and another ground conductor 22 routed through ground current sensor 24 to system ground 21 (hereinafter referred to as system ground). In accordance with the invention, the ground current sensor 24 senses the magnitude of ground current in ground current path 15 and creates a control signal in response to the ground current exceeding a predetermined threshold. The control signal so generated is routed to controller 26 which, in turn, controls ground current latch 20 by interrupting the ground connection between shield ground conductor 19 and system ground 21. Alternative to latching open such ground connection, another embodiment of the present invention limits the ground current to a maximum predetermined level. In this alternate embodiment, ground current latch block 20 is replaced be a ground current limiter 30. Thus, the shield ground safety device may be implemented by the circuit block 17 of FIG. 1C (latch) or by the circuit block 17A of FIG. 1D (limiter).

Figure 2:
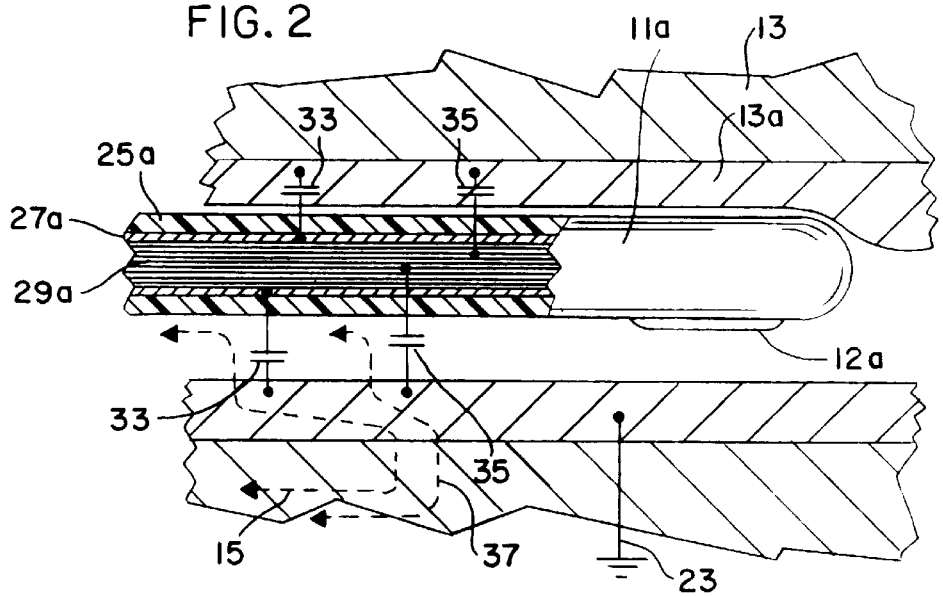
FIG. 2 is a partial cross sectional side view of the end of an ultrasound transducer probe having a first internal construction.

FIG. 2 is a partial cross sectional view showing the tip of an ultrasound transducer probe 11a having a transducer window 12a laterally of the tip of the probe 11a for viewing the interior, for example, of an artery 13a of a body 13. As was explained above, the outer housing 25a of probe 11a is made of dielectric material to physically and electrically space the ground shield 27a of probe 11a from the body 13, 13a. The tubular conductive shield 27a encloses a number of micro coaxial conductors 29a, or other multiple-conductor means routed to the transducer at the tip of the probe behind window 12a.

FIG. 2 shows a representation of several capacitive coupling paths between the probe 11a and the body 13, 13a in the form of capacitances 35 between the inner conductors 29a of the probe 11a and the body, and capacitances 33 between the ground shield 27a of the probe 11a and the body 13, 13a. The distributive capacitances 33, 35 are responsible for the flow of unwanted AC currents in the signal conductors 29a through AC current path 37, and the ground shield 27a through AC current path 15.

Figure 3:
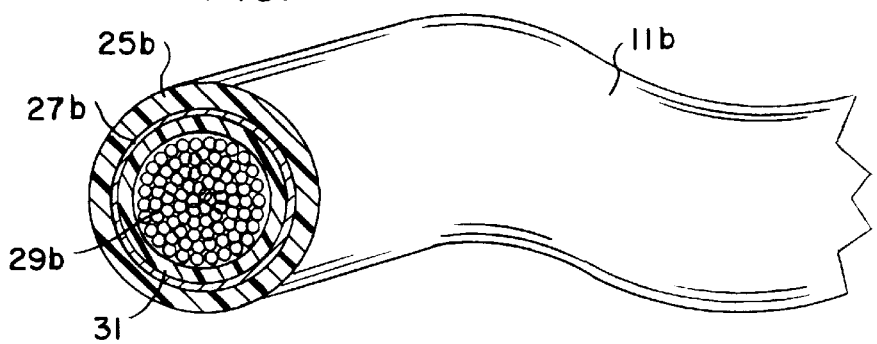
FIG. 3 is a cross sectional end view of a catheter probe showing a second internal construction.

The cross sectional view of a portion of a thin catheter probe 11b in FIG. 3 illustrates the problem associated with the prior art attempt to solve ground shield current problems by increasing the thickness of the dielectric layer 25b on the outside of braided ground shield 27b. The catheter probe 11b carries a phased array ultrasound probe 12b at its tip (see FIG. 4A). Such catheters may be inserted into a major vein or artery and threaded through the vascular system up to a length of 1 meter to image the interior of the heart. The catheter consists of an outer insulating jacket 25b surrounding a braided steel tube 27b used both for mechanical strength and electrical shielding. Inside the braid 27b is another insulating layer 31 surrounding the wiring 29b electrically connecting the ultrasound transducer to the ultrasound system 1. It can be appreciated that making the outer insulating jacket 25b thicker is difficult while attempting to maintain a diameter of less than about 4 mm, and providing space for conductors and articulating control lines.

As mentioned above, a typical catheter-based ultrasound probe may be well shielded from electrical noise with its shield braid, e.g. 27b, connected to the ground system and chassis 21, but would pass dangerous leakage current under a system single-fault condition. Conversely, such a probe with its shield braid, e.g. 27b, disconnected is safe under a single-fault condition but suffers greatly from coupled electrical noise.

Figure 1B:
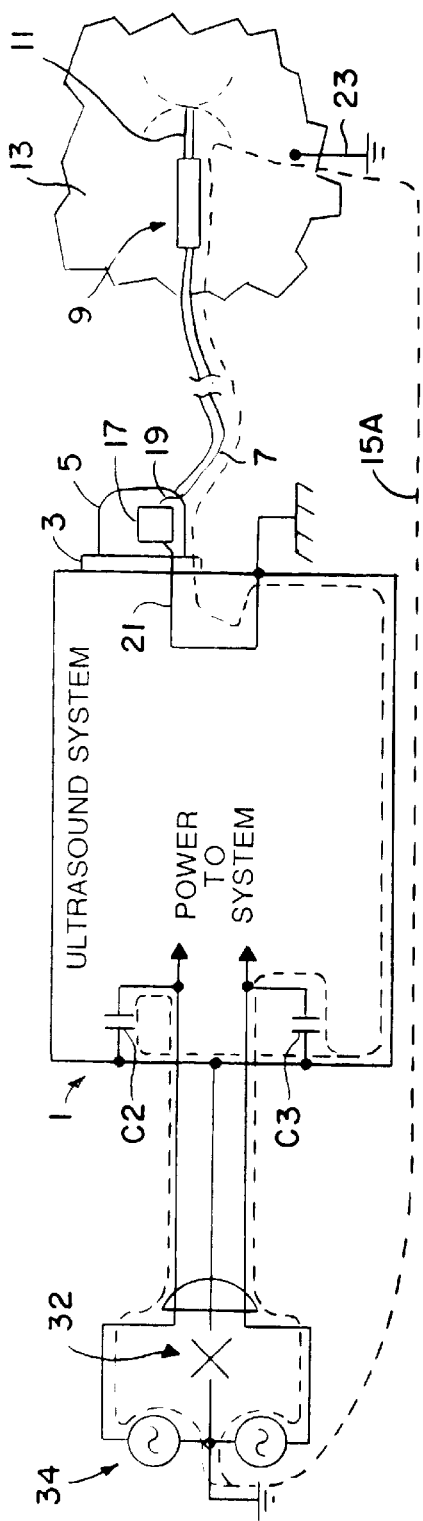
FIG. 1B illustrates an alternate placement for the shield ground safety device and the ground path for a typical ultrasound transducer system.

FIG. 1B shows, more explicitly than FIG. 1A, the source of the leakage current in the shield ground current path of a typical ultrasound transducer system in which power is supplied by a center grounded balanced power line 34 (e.g., a 220 volt power source) with the safety ground line between the power source 34 and the ultrasound system console lifted. A ground path nevertheless exists as shown by ground current path 15A passing through the ultrasound system internal power supply capacitances C2 and C3.

FIG. 1B also shows a different location for the shield ground safety device circuit 17 of the present invention than that illustrated in FIG. 1A. In FIG. 1A, the shield ground safety device circuit 17 is located in the Ultrasound system console 1, while in the preferred embodiment of FIG. 1B, it is housed within the transducer connector 5.

Figure 4A:
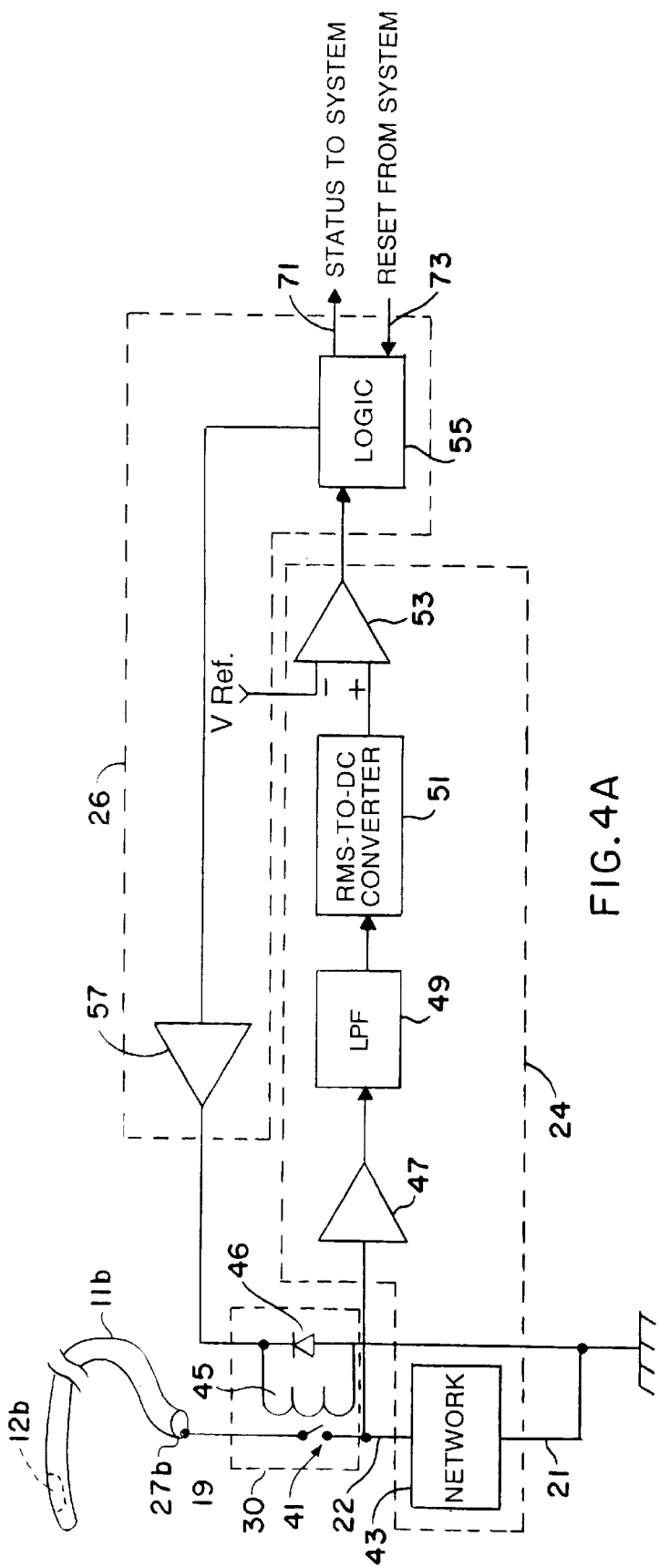
FIG. 4A is a schematic block diagram of the electronic components for implementing one embodiment of the invention, the circuitry of FIG. 4A including a catheter probe also schematically shown.

FIG. 4A shows a block diagram for a preferred embodiment of the invention. The major function blocks of FIG. 1A are shown in more detail in FIG. 4A. This configuration follows the construction described above for an active network that is transparent to ground current signals if they are lower than a certain predetermined threshold, but rapidly latches in an "open" state when sensing a ground current signal exceeding the threshold.

The circuit configuration of FIG. 4A solves the high "on" resistance problem in Kroll's apparatus. The transducer outer braid shield 27b is connected to system ground 21 through relay contacts 41 (when closed) and current sensing network 43. Contacts 41 are normally open for safety reasons and are closed during normal operation of the system (see below).

Figure 4B:
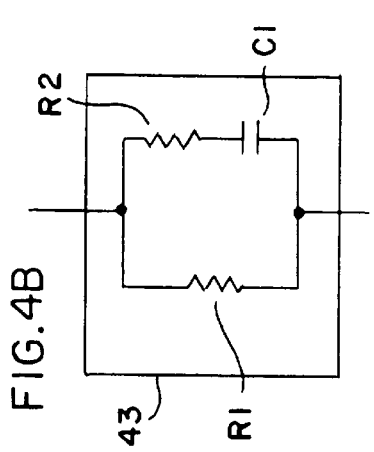
FIG. 4B is a schematic of the network of FIG. 4A.

Current sensing network 43 (FIG. 4B) implements the high-frequency rolloff specified in UL544, Section 42.3.3. It has an impedance of 100 ohms at DC, rolling off at 6 dB/octave starting at 1 kHz to a minimum impedance of about 1 ohm at and above 100 kHz. A simple 1 ohm resistor may be used in place of network 43, but the network reduces the high gain requirement for amplifier 47 by providing a larger signal at its input. Using a resistor value of 100 ohms for R1, a resistor of 1 ohm for R2, and a capacitor of 1.6 82 F for C1, the impedance rolloff provides the low impedance (about 1 ohm) required for effective shielding above 100 kHz. Clearly, the impedance of network 43 can be scaled to provide any useful impedance levels, with R1 typically in the range of 10 to 1000 ohms.

The ultrasound system supplies DC power to the rest of the circuit of FIG. 4A upon connection of the probe 11b to the system. The circuitry for implementing this "power supply" function is not shown, as it could be easily configured by a person of ordinary skill in the art. When the probe 11b is plugged in and DC power is applied, the logic block 55 boots up and sends a signal to the relay driver 57 which, in turn, energizes the coil of relay 45 and closes the relay contacts 41. The logic block 55 also reports its status ("safe" in this case) to the imaging system over output line 71.

The network 43 continuously senses the current in the ground shield connection for all frequencies of concern. Network 43 has a value of about 1 ohm for frequencies over 100 kHz which is effective for shunting noise currents to system ground. Network 43 has a value of about 100 ohms at frequencies below about 1 khz. The voltage across the network 43 is proportional to this current, e.g., at low frequencies, the threshold current of 20 $\mu$A induces a potential of 2 mV.

The logic block 55 can also include a power-on self-test feature (not shown) that injects a test current into the sensing network 43 before closing relay contacts 41 to ensure proper operation.

The resultant potential across sensing network 43 is amplified by a gain stage 47 and low-pass filtered by low pass filter 49 before being sent by an rms-to-DC converter 51. Amplifier stage 47 has a gain in the range of 50 to 500 and is typically 100 when using a 100 ohm DC impedance described for the sensing network 43.

The low pass filter 49 may be used to add frequency dependent characteristics, or may eliminate "nuisance tripping" from high frequency noise, or may be eliminated altogether. The gain stage 47 has a very low input offset voltage. Such a device is available as the MAX400 operational amplifier from Maxim Integrated Products, Sunnyvale, Calif. A suitable rms-to-DC converter is available as the MX636 from Maxim Integrated Products, Sunnyvale, Calif.

The DC output of the converter 51 is sensed by a comparator 53 (for example the MAX985 comparator from Maxim Integrated Products, Sunnyvale, Calif.) in such a way that, if the rms current flowing through the sensing network 43 exceeds 20 $\mu$A (or a level slightly below 20 $\mu$A), the logic block 55 rapidly sends a signal to the relay driver 57 to open the contacts 41 of relay 45 and disconnect the probe shield 27b (i.e., line 19) from system ground 21.

The voltage reference for comparator 53 may be provided by any one of many commonly used constant voltage circuits.

A diode 46 shunts reverse current through the coil of relay 45 when its magnetic field collapses, such diodes typically being connected across relay coils in a known manner.

Upon the circuit of FIG. 4A sensing a ground current exceeding 20 μA, in addition to opening relay 45, the logic block 55 also sends a message to the system; and the system, in turn, may display a warning on its display screen. The circuit of FIG. 4A may be reset by momentarily disconnecting the probe 11b from the ultrasound system 1 or, alternatively, by inputting instructions from the ultrasound system on input line 73 to reset the logic block 55.

Figure 5:
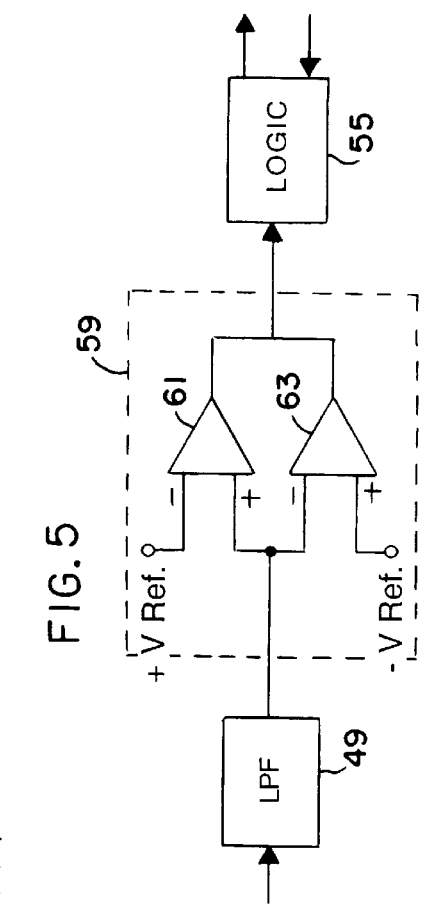
FIG. 5 shows an alternative circuit for the rms-to-DC converter of FIG. 4A.

FIG. 5 shows an alternative scheme for detecting a high ground current condition in network 43. All circuitry is the same as in FIG. 4A, except that the rms-to-DC converter 51 and the comparator 53 of FIG. 4A are replaced by a window comparator circuit 59. This embodiment detects when the instantaneous current through network 43 exceeds any positive or negative value exceeding set positive and negative reference thresholds, respectively, while the embodiment of FIG. 4A essentially detects the rms current exceeding a threshold.

The window comparator 59 consists of a pair of voltage references, +V Ref. and −V Ref., and a pair of simple comparators of the type used in FIG. 4A. Comparator 61 is configured to detect an instantaneous positive voltage on its + input greater than +V Ref. Comparator 63 is configured to detect an instantaneous negative voltage on its—input greater than −V Ref. Comparator 61 is thus triggered by excessive positive current in network 43, while comparator 63 is triggered by excessive negative current in network 43. Detection of either positive or negative ground current values in excess of 20 μA will trigger logic block 55 and create the aforementioned relay drive signal for relay driver 57 and the status signal to the system on output line 73 (in this case, "unsafe").

Figure 1D:
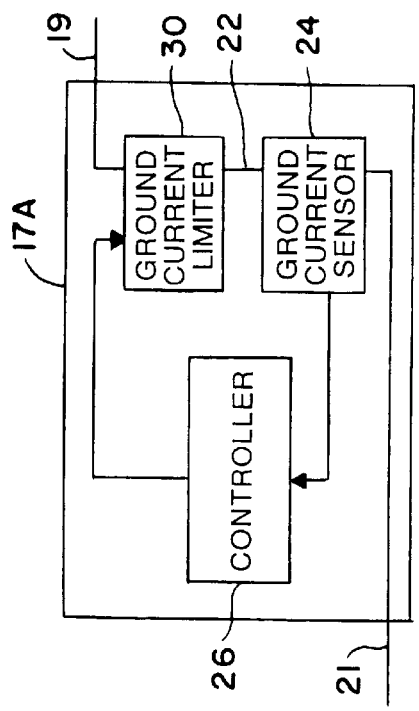
FIG. 1D shows the major components of another embodiment of shield ground safety device.
Figure 6:
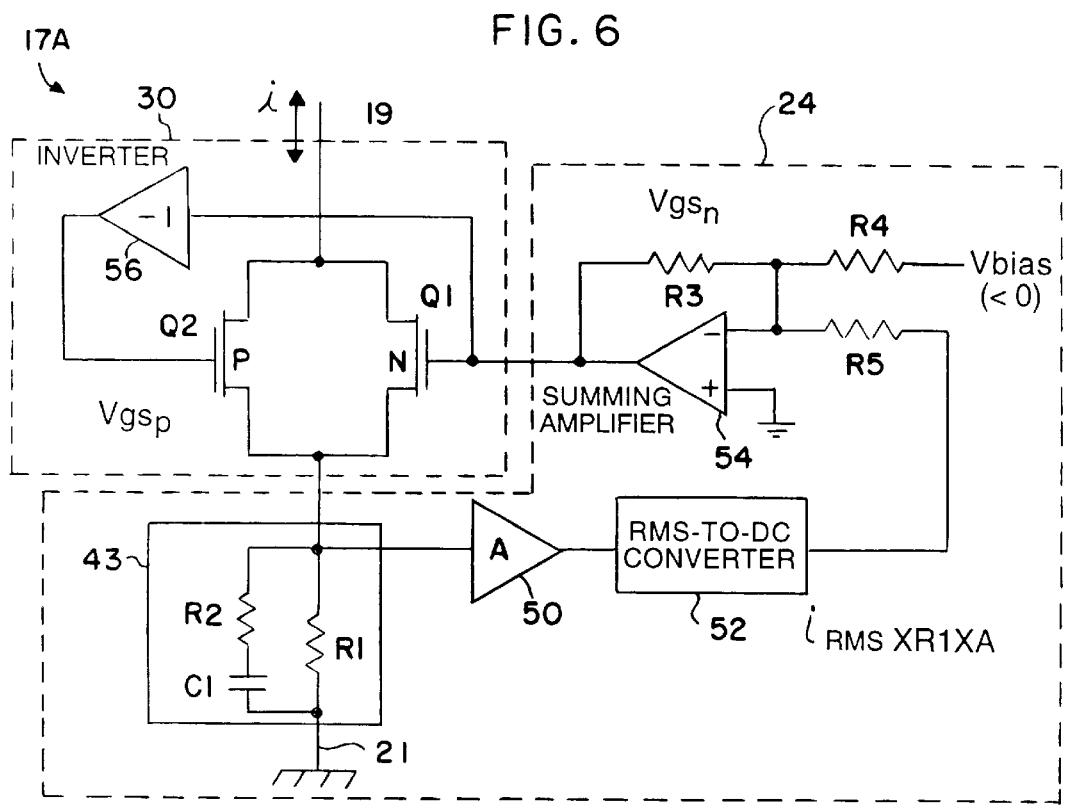
FIG. 6 is a schematic diagram showing an implementation of the ground current limiter block of FIG. 1D.

FIG. 6 is a schematic of one implementation of the ground current limiter 30 of FIG. 1D. The AC ground current "i" on ground line 19 normally passes through sensing network 43 to develop a voltage across network 43. This voltage is amplified in amplifier 50, and the amplified rms value is converted to DC voltage by rms-to-DC converter 52 and applied to the negative input of summing amplifier 54. Summing amplifier 54 has a negative reference potential, developed by the voltage divider network R3, R4, and R5, resulting in a positive output voltage $Vgs_n$ applied to the gate of n-channel power MOSFET Q1 biasing it to an "on" state. The gate-to-source voltage $Vgs_n$ is inverted in unity gain inverter 56 and applied to the gate of the p-channel power MOSFET Q2 biasing it to an "on" state. Because the ground currents to be dealt with are alternating currents, current limiter 30 must present a low impedance to current flow in either direction through it. Thus, the n-channel device Q1 will present a low impedance to current "i" in one direction, and the p-channel device Q2 will present a low impedance to current "i" in the opposite direction. In this condition of the circuit of FIG. 6, the two power MOSFETS Q1 and Q2 represent a very low resistance of about 1 ohm for a ground current "i"≦20 μA.

In the event ground current "i" tends to exceed 20 μA, the DC output of rms-to-DC converter 52 brings the voltage at the negative input of summing amplifier 54 above ground to cause the output of summing amplifier 54 to swing negative, reducing the current through Q1, and Q2 via inverter 56, and increasing the drain-to-source resistances, thereby reducing the current "i" passing through sensor network 43., i.e. keeping the ground current "i" to ≦20 μA For so long as ground current "i"≦20 μA, the extremely low drain-to-source resistances of Q1 and Q2 make the ground current limiter block 30 virtually transparent to shield ground current flow through ground line 19 to system ground 21. However, as ground current "i" approaches and attempts to exceed 20 μA, the circuit of FIG. 6 inserts higher effective resistance between ground line 19 and ground line 22 (FIG. 1D), and thus does not allow ground current "i" to exceed 20 μA.

More specifically, the following conditions are suggested for the circuit of FIG. 6.

Output of rms-to-DC converter $52=i_{nk} \times R1 \times A$ for frequencies ≦1 kHz.

Choose Q1 n-channel power MOSFET with:

$R_{DS(on)}$≦about 1 ohm, $V_T = V_{Tn}$=+1 to +2 volts,

Breakdown $V_{DSS}$, $V_{DGR}$≧400 volts.

Choose Q2 p-channel power MOSFET with:

$R_{DS(on)}$≦about 1 ohm, $V_T = V_{TP}$=−2 to −1 volts,

Breakdown $V_{DSS}$, $V_{DGR}$≧400 volts.

Adjust Resistors R3–R5 such that:

$Vgs_n = V_{Tn}$+(Va volts) For $i_{rms}$≦10 μA $Vgs_n = V_{Tn}$—(Va volts) For $i_{rms}$≧20 μA Where Va is chosen dependent upon the desired sensitivity of the circuit.

Unity Gain Inverter 56 provides a similar but inverted gate voltage to Q2.

Q1 source: MTP5N4OE from Motorola, Inc. of Phoenix, Ariz.

Q2 source: MTP2P50E from Motorola, Inc. of Phoenix, Ariz.

Figure 1C:
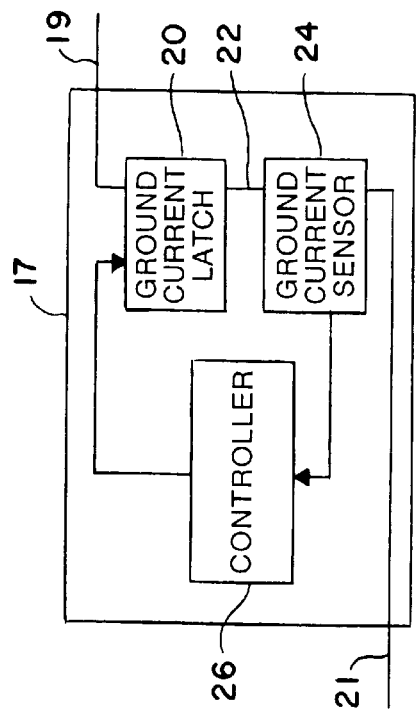
FIG. 1C shows the major components of one embodiment of shield ground safety device.

The circuit of FIG. 6 and the embodiment of ground current limiter 17A of FIG. 1D are preferred over the "latch open" function of FIGS. 1A, 1B, and 1C, since using the former maintains some level of operation of the ultrasound transducer system, while the latter, although protecting the patient from potentially dangerous ground currents, essentially makes the system useless until it is reset. Moreover, using the former solution, normal operation is instantaneously restored after a single fault condition subsides, while the latter solution requires some delay time, and perhaps a test procedure to take place before a "reset" signal on line 73 is sent back to logic block 55 (FIG. 4A).

It will be clear to those skilled in the art that the current sensing scheme described above could also be configured to trigger other functions in, or associated with, an ultrasound system. FIGS. 7 and 8 show such a system. An accessory power outlet 75 on the ultrasound system console may be provided, into which the power plug of and external patient-connected equipment is inserted (or the external equipment hardwired thereto). The current latching or current limiting arrangement of the present invention may be employed to disconnect the accessory power outlet instead of, or in addition to, disconnecting the ultrasound probe ground.

In the arrangement of FIGS. 7 and 8, the controller 26A, in ground current limiter 17A, controls ground current limiter 20 to limit current through the probe shield ground as before, but controller 26A also disables an accessory power outlet 75 via a double-pole relay 76. The switched accessory power outlet 75 is used to supply power to an external patient-connected equipment 77. A fault in the external patient-connected equipment 77 may cause current to flow through the patient via its ground shielded connection 78 and back to ground through the ultrasound probe 9. In this instance, the controller 26A signals relay 76 via output 79, causing the contacts 76A to open and disable the external equipment 77. The relay could, if desired, be a three-pole device 77B (FIG. 9) to lift the ground connection 77A of the external equipment as well. Alternatively, the relay 76B of FIG. 9 may have only a single switched contact which lifts only the ground connection 77A and leaves the power lines connected.

In this description, a threshold ground current of 20 μA has been used as the threshold value. To ensure against ground currents exceeding a safe level of 20 μA, a small margin below the 20 82 A level may be set. For example, a threshold of between 15 and 20 μA may be set, dependent upon the precision of circuit components chosen and circuit design tolerances.

While only certain embodiments of the invention have been set forth above, alternative embodiments and various modifications will be apparent from the above description and the accompanying drawing to those skilled in the art. For example, for certain equipment-to-patient connections defined in the UL 544 specifications, allowed ground leakage currents may be as high as 50 μA. It would be within the skill of the artisan to adjust the component values in network 43 to set the threshold in the range of 45 to 50 μA, if desired. As another example, FIG. 3 shows the wiring 29b internal to the probe as a bundle of micro coaxial conductors. The invention is not to be so limited. It will be understood that any of a variety of configuration of multiple conductors can be used instead of the micro coaxial conductors shown, such as flex circuits, stacked flex circuits, folded flex circuits, twisted pairs, and insulated wiring, to name a few. Such multiple conductor configurations may be provided with a surrounding shield ground, or one or more ground conductors among the multiple conductors. As yet another example, the concepts of the present invention may be implemented in principle in a variety of electronic equipment applications, i.e., the invention is not limited to ultrasound shielding applications. These and other alternatives are considered equivalents and within the spirit and scope of the present invention.

What is claimed is:

1. A shield ground safety device for a medical ultrasound probe connected to an ultrasound system by a shielded cable, the probe having a probe shield, and the shielded cable having a cable shield coupling the probe shield to system ground in an ultrasound system, said safety device comprising:

a current limiter inserted in series in a ground current path which includes said probe shield, said cable shield, and system ground, said current limiter limiting current passing therethrough in a first state, and passing current therethrough unaltered in a second state;

a current sensor for outputting a control signal upon detecting the occurrence of ground current in said ground current path exceeding a predetermined value; and a controller, responsive to said control signal from said current sensor, for setting said current limiter to said first state when current in said ground current path exceeds said predetermined value.

2. The shield ground safety device as claimed in claim 1, wherein said controller is responsive to said control signal from said current sensor for setting said current limiter to said second state when current in said ground current path is less than said predetermined value.

3. The shield ground safety device as claimed in claim 1, wherein said predetermined current value is in the range of 15 to 20 microamps.

4. The shield ground safety device as claimed in claim 1, wherein said current sensor has an input impedance in the range of about 0.1 to 10 ohms for operating frequencies at and above 100 kHz.

5. The shield ground safety device as claimed in claim 1, wherein probe-shield to system-ground impedance is in the range of about 0.1 to 10 ohms for operating frequencies at and above 100 kHz when said current limiter is in said second state.

6. The shield ground safety device as claimed in claim 1, wherein said circuit sensor detects AC ground currents, and comprises:

an input impedance network for developing an AC ground voltage signal proportional to said AC ground current;

an rms-to-DC converter for converting said AC ground voltage signal to a DC signal; and a comparator receiving said DC signal, comparing said DC signal to a reference voltage, and conditioning said control signal outputted to said controller for setting said current limiter to said first state when said DC signal exceeds said reference voltage corresponding to when said ground current exceeds said predetermined value.

7. The shield ground safety device as claimed in claim 1, wherein:

said current sensor detects AC ground current in said ground current path, and comprises an AC ground-current to DC-signal converter outputting a DC signal proportional to the magnitude of said AC ground current; and said controller sets said current limiter to said first state when said DC signal exceeds a predetermined DC level.

8. The shield ground safety device as claimed in claim 1, wherein:

said current sensor detects AC ground current in said ground current path, and comprises a window comparator outputting a trigger signal when said AC ground current exceeds a predetermined absolute magnitude level; and said controller sets said current limiter to said first state upon receiving a trigger signal from said current sensor.

9. The shield ground safety device as claimed in claim 1, wherein:

said current sensor detects AC ground current in said ground current path, and comprises a low pass filter for inhibiting generation of said control signal when the frequency of said AC ground current is above a predetermined cutoff frequency.

10. The shield ground safety device as claimed in claim 1, wherein said circuit sensor detects AC ground currents, and comprises:

an input impedance network for developing an AC ground voltage signal proportional to said AC ground current;

a window comparator comprising a positive threshold detector outputting a trigger signal when said AC ground current voltage signal exceeds a predetermined positive threshold voltage, and further comprising a negative threshold detector outputting a trigger signal when said AC ground voltage signal exceeds a predetermined negative threshold voltage; and said window comparator conditions said control signal outputted to said controller for setting said current limiter to said first state upon the occurrence of said window detector outputting a trigger signal.

11. The shield ground safety device as claimed in claim 7, wherein said impedance network is an RC network having a DC resistance in the range of 10 to 1000 ohms and rolling off at 6 dB/octave starting at 1 kHz to a minimum impedance of about 0.1 to 10 ohms for operating frequencies at and above 100 kHz.

12. A ground safety device for a medical ultrasound probe connected to an ultrasound system by a grounded cable, the probe having a probe ground, and the grounded cable having a cable ground coupling the probe ground to system ground in an ultrasound system, said safety device comprising:

an active network that is transparent to ground current signals if they are lower than a certain prescribed threshold, and limits ground current signals which exceed the threshold.

13. A ground safety device for a medical ultrasound probe connected to an ultrasound system by a grounded cable, the probe having a probe ground, and the grounded cable having a cable ground coupling the probe ground to system ground in an ultrasound system, said safety device comprising:

an active network that is transparent to ground current signals having an alternating current content substantially above a predetermined cutoff frequency, but limits ground current signals with alternating current content below the cutoff frequency.

14. A ground safety device for a medical ultrasound probe connected to an ultrasound system by a grounded cable, the probe having a probe ground, and the grounded cable having a cable ground coupling the probe ground to system ground in an ultrasound system, said safety device comprising:

an active network that is transparent to ground current signals having an AC content exclusively above a predetermined cutoff frequency, but latches in an "open" state when a ground current signal below said cutoff frequency exceeds a predetermined value.

15. A shield ground safety device for a medical ultrasound probe connected to an ultrasound system by a shielded cable, the probe having a probe shield, and the shielded cable having a cable shield coupling the probe shield to system ground in an ultrasound system, said safety device comprising:

a current latch inserted in series in a ground current path which includes said probe shield, said cable shield, and system ground, said current latch opening said ground current path in a first state, and passing current therethrough unaltered in a second state;

a current sensor for detecting when ground current in said ground current path exceeds a predetermined value, and outputting a control signal; and a controller, responsive to said control signal from said current sensor, for setting said current latch to said first state when current in said ground current path exceeds said predetermined value.

16. The shield ground safety device as claimed in claim 15, wherein said controller is responsive to said control signal from said current sensor for setting said current latch to said second state when current in said ground current path is less than said predetermined value.

17. The shield ground safety device as claimed in claim 15, wherein said predetermined current value is 20 microamps.

18. The shield ground safety device as claimed in claim 15, wherein said current sensor has an input impedance in the range of about 0.1 to 10 ohms for operating frequencies at and above 100 kHz.

19. The shield ground safety device as claimed in claim 15, wherein probe-shield to system-ground impedance is in the range of about 0.1 to 10 ohms for operating frequencies at and above 100 kHz when said current latch is in said second state.

20. The shield ground safety device as claimed in claim 15, wherein said circuit sensor detects AC ground currents, and comprises:

an input impedance for developing an AC ground voltage signal proportional to said AC ground current;

an rms-to-DC converter for converting said AC ground voltage signal to a DC signal; and a comparator receiving said DC signal, comparing said DC signal to a reference voltage, and conditioning said control signal outputted to said controller for setting said current latch to said first state when said DC signal exceeds said reference voltage corresponding to when said ground current exceeds said predetermined value.

21. The shield ground safety device as claimed in claim 15, wherein said circuit sensor detects AC ground currents, and comprises:

an input impedance network for developing an AC ground voltage signal proportional to said AC ground current;

a window comparator comprising a positive threshold detector outputting a trigger signal when said AC ground current voltage signal exceeds a predetermined positive threshold voltage, and further comprising a negative threshold detector outputting a trigger signal when said AC ground voltage signal exceeds a predetermined negative threshold voltage; and said window comparator conditions said control signal outputted to said controller for setting said current latch to said first state upon the occurrence of said window detector outputting a trigger signal.

22. The shield ground safety device as claimed in claim 15, wherein:

said current sensor detects AC ground current in said ground current path, and comprises an AC ground-current to DC-signal converter outputting a DC signal proportional to the magnitude of said AC ground current; and said controller sets said current latch to said first state when said DC signal exceeds a predetermined DC level.

23. The shield ground safety device as claimed in claim 15, wherein:

said current sensor detects AC ground current in said ground current path, and comprises a window comparator outputting a trigger signal when said AC ground current exceeds a predetermined absolute magnitude level; and said controller sets said current latch to said first state upon receiving a trigger signal from said current sensor.

24. The shield ground safety device as claimed in claim 15, wherein:

said current sensor detects AC ground current in said ground current path, and comprises a low pass filter for inhibiting generation of said control signal when the frequency of said AC ground current is above a predetermined cutoff frequency.

25. The shield ground safety device as claimed in claim 15, wherein said current latch is an electrical switching device having a normally open switch condition when disabled defining said first state, and a switch closed condition when enabled defining said second state.

26. A ground safety device for a medical ultrasound probe connected to an ultrasound system by a grounded cable, the probe having a probe ground, and the grounded cable having a cable ground coupling the probe ground to system ground in an ultrasound system, said safety device comprising:

an active network transparent to ground current signals if they are lower than a certain prescribed threshold, and disconnecting said probe ground from said system ground for ground current signals which exceed the threshold.

27. A ground safety device for a medical ultrasound probe connected to an ultrasound system by a grounded cable, the probe having a probe ground, and the grounded cable having a cable ground coupling the probe ground to system ground in an ultrasound system, said safety device comprising:

an active network that is transparent to ground current signals if they are lower than a certain prescribed threshold, but latches in an "open" state when a ground current signal exceeds the threshold.

28. A ground safety device for a medical ultrasound probe connected to an ultrasound system by a grounded cable, the probe having a probe ground, and the grounded cable having a cable ground coupling the probe ground to system ground in an ultrasound system, said safety device comprising:

an active network transparent to ground current signals having an alternating current content substantially above a predetermined cutoff frequency, and disconnecting ground current signals with alternating current content below the cutoff frequency.

29. A ground safety device for a medical ultrasound probe connected to an ultrasound system by a grounded cable, the probe having a probe ground, and the grounded cable having a cable ground coupling the probe ground to system ground in an ultrasound system, said safety device comprising:

an active network transparent to ground current signals having an AC content exclusively above a predetermined cutoff frequency, and latching in an "open" state when a ground current signal below said cutoff frequency exceeds a predetermined value.

30. A shield ground safety device for an ultrasound system comprising a medical ultrasound probe in contact with a body and connected to the ultrasound system by a shielded cable, the probe having a probe shield, and the shielded cable having a cable shield coupling the probe shield to system ground in the ultrasound system, the ultrasound system supplying power to an external patient-connected equipment unit having contact with said body and having a shield ground and power connection with said ultrasound system, said safety device comprising:

a current limiter inserted in series in a ground current path which includes said probe shield, said cable shield, and system ground, said current limiter limiting current passing therethrough in a first state, and passing current therethrough unaltered in a second state;

a current sensor for outputting a control signal upon detecting the occurrence of ground current in said ground current path exceeding a predetermined value; and a connection interrupt device for interrupting said power connection from said ultrasound system to said external patient-connected equipment unit upon receiving an interrupt drive signal;

a controller, responsive to said control signal from said current sensor, for producing a current limiter drive signal routed to said ground current limiter for setting said ground current limiter to said first state when current in said ground current path exceeds said predetermined value, said controller further producing an interrupt drive signal, responsive to said control signal from said current sensor, said interrupt drive signal routed to said connection interrupt device for interrupting said power connection from said ultrasound system to said external patient-connected equipment unit.

31. The shield ground safety device as claimed in claim 30, wherein said connection interrupt device is adapted to interrupt said shield ground of said external patient-connected equipment unit; and said interrupt drive signal interrupts said ground connection from said ultrasound system to said external patient-connected equipment unit.

32. A shield ground safety device for an ultrasound system comprising a medical ultrasound probe in contact with a body and connected to the ultrasound system by a shielded cable, the probe having a probe shield, and the shielded cable having a cable shield coupling the probe shield to system ground in the ultrasound system, the ultrasound system supplying power to an external patient-connected equipment unit having contact with said body and having a shield ground and power connection with said ultrasound system, said safety device comprising:

a current limiter inserted in series in a ground current path which includes said probe shield, said cable shield, and system ground, said current limiter limiting current passing therethrough in a first state, and passing current therethrough unaltered in a second state;

a current sensor for outputting a control signal upon detecting the occurrence of ground current in said ground current path exceeding a predetermined value; and a connection interrupt device for interrupting said ground connection from said ultrasound system to said external patient-connected equipment unit upon receiving an interrupt drive signal;

a controller, responsive to said control signal from said current sensor, for producing a current limiter drive signal routed to said ground current limiter for setting said ground current limiter to said first state when current in said ground current path exceeds said predetermined value, said controller further producing an interrupt drive signal, responsive to said control signal from said current sensor, said interrupt drive signal routed to said connection interrupt device for interrupting said ground connection from said ultrasound system to said external patient-connected equipment unit.

33. A shield ground safety device for limiting ground currents flowing between a first electronic equipment unit and a second electronic equipment unit connected by a shielded cable having a cable shield coupled to system ground in said first electrical equipment unit, said safety device comprising:

a current limiter inserted in series in a ground current path which includes said cable shield and system ground, said current limiter limiting current passing therethrough in a first state, and passing current therethrough unaltered in a second state;

a current sensor for outputting a control signal upon detecting the occurrence of ground current in said ground current path exceeding a predetermined value; and a controller, responsive to said control signal from said current sensor, for setting said current limiter to said first state when current in said ground current path exceeds said predetermined value.

34. The shield ground safety device as claimed in claim 33, wherein said controller is responsive to said control signal from said current sensor for setting said current limiter to said second state when current in said ground current path is less than said predetermined value.

35. The shield ground safety device as claimed in claim 33, wherein said predetermined current value is in the range of 15 to 20 microamps.

36. The shield ground safety device as claimed in claim 33, wherein said current sensor has an input impedance in the range of about 0.1 to 10 ohms for operating frequencies at and above 100 kHz.

37. A ground safety device for a medical ultrasound probe connected to an ultrasound system by a cable, the probe having a ground conductor, the cable having a ground conductor coupling the probe ground conductor to system ground in an ultrasound system, said ground safety device comprising:

a current limiter inserted in series in a ground current path which includes said probe ground conductor, said cable ground conductor, and system ground, said current limiter limiting current passing therethrough in a first state, and passing current therethrough unaltered in a second state;

a current sensor for outputting a control signal upon detecting the occurrence of ground current in said ground current path exceed current sensor, for setting said current limiter to said first state when current in said ground current path exceeds said predetermined value.

38. The ground safety device as claimed in claim 37, wherein said controller is responsive to said control signal from said current sensor for setting said current limiter to said second state when current in said ground current path is less than said predetermined value.

39. The ground safety device as claimed in claim 37, wherein said predetermined current value is in the range of 15 to 20 microamps.

40. The ground safety device as claimed in claim 37, wherein said current sensor has an input impedance in the range of about 0.1 to 10 ohms for operating frequencies at and above 100 kHz.

41. A ground safety device for a medical ultrasound probe connected to an ultrasound system by a grounded cable, the probe having a ground conductor, the cable coupling the probe ground conductor to system ground in an ultrasound system, said safety device comprising:

a current latch inserted in series in a ground current path which includes said probe ground conductor, said cable ground conductor, and system ground, said current latch opening said ground current path in a first state, and passing current therethrough unaltered in a second state;

a current sensor for detecting when ground current in said ground current path exceeds a predetermined value, and outputting a control signal; and a controller, responsive to said control signal from said current sensor, for setting said current latch to said first state when current in said ground current path exceeds said predetermined value.

42. The ground safety device as claimed in claim 41, wherein said controller is responsive to said control signal from said current sensor for setting said current latch to said second state when current in said ground current path is less than said predetermined value.

43. The ground safety device as claimed in claim 41, wherein said predetermined current value is 20 microamps.

44. The ground safety device as claimed in claim 41, wherein said current sensor has an input impedance in the range of about 0.1 to 10 ohms for operating frequencies at and above 100 kHz.

* * * * *

UNITED STATES PATENT AND TRADEMARK OFFICE
CERTIFICATE OF CORRECTION

PATENT NO. : 5,995,348
DATED : November 30, 1999
INVENTOR(S) : Dermot McCartan et al.   Page 1 of 2

It is certified that error appears in the above-identified patent and that said Letters Patent is hereby corrected as shown below:

On the Title Page

In column 1, item [75], please change "Dublin" to --Sunnyvale--.

In column 7, lines 56 and 64, please change "$\leqq$" to --$\leq$--.

In column 8, line 9, please change "$i_{nk}$" to --$i_{rms}$--.

In column 8, lines 10 and 12, please change "$\leqq$" to --$\leq$--.

In column 8, line 13, please change "$\geqq$" to --$\geq$--.

In column 8, line 15, please change "$\leqq$" to --$\leq$--.

In column 8, line 16, please change "$\geqq$" to --$\geq$--.

In column 8, line 18, please change "$\leqq$" to --$\leq$--.

In column 8, line 19, please change "—" to -- - -- (hyphen); and "$\geqq$" to --$\geq$--.

UNITED STATES PATENT AND TRADEMARK OFFICE
CERTIFICATE OF CORRECTION

PATENT NO. : 5,995,348
DATED : November 30, 1999
INVENTOR(S) : Dermot McCartan et al.

It is certified that error appears in the above-identified patent and that said Letters Patent is hereby corrected as shown below:

In column 8, line 47, please change "and" to --an--.

In column 9, line 6, please change "82" to --µA--.

In claim 37, line 15, please change "exceed" to --exceeding--.

Signed and Sealed this

Tenth Day of April, 2001

Attest:

NICHOLAS P. GODICI

Attesting Officer     Acting Director of the United States Patent and Trademark Office